(12) United States Patent
Yeom et al.

(10) Patent No.: US 8,709,511 B2
(45) Date of Patent: Apr. 29, 2014

(54) EXTERNAL PREPARATION COMPOSITION FOR SKIN COMPRISING GINSENG FLOWER OR GINSENG SEED EXTRACTS

(75) Inventors: Myeong Hun Yeom, Yongin-si (KR); Jin Young Lee, Seoul (KR); Jung Sun Hwang, Yongin-si (KR); Nok Hyun Park, Yongin-si (KR); Jun Seong Park, Suwon-si (KR); Duck Hee Kim, Seoul (KR); Han Kon Kim, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 12/997,822

(22) PCT Filed: Apr. 28, 2009

(86) PCT No.: PCT/KR2009/002206
§ 371 (c)(1),
(2), (4) Date: Dec. 13, 2010

(87) PCT Pub. No.: WO2009/151212
PCT Pub. Date: Dec. 17, 2009

(65) Prior Publication Data
US 2011/0085996 A1 Apr. 14, 2011

(30) Foreign Application Priority Data

Jun. 13, 2008 (KR) .................. 10-2008-0055798
Jun. 16, 2008 (KR) .................. 10-2008-0056541
Dec. 9, 2008 (KR) .................. 10-2008-0124479
Dec. 9, 2008 (KR) .................. 10-2008-0124500

(51) Int. Cl.
*A61K 36/254* (2006.01)
(52) U.S. Cl.
USPC .......................................... 424/728; 424/725
(58) Field of Classification Search
None
See application file for complete search history.

(56) References Cited

FOREIGN PATENT DOCUMENTS

| KR | 84-000561 | 4/1984 |
| KR | 10-2008-0044959 | 5/2008 |
| WO | WO 2007/007255 A2 | 1/2007 |

OTHER PUBLICATIONS

Dooley et al., "Development of an in vitro promary screen for skin depigmentation and antimelanoma agents", Sin Pharmacol. (1994) 7: pp. 188-200.*
Yoshikawa et al., "Structures of new dammarane-type triterpene saponins from the flower buds of *Panax notoginseng* and Hepatoproctive effects of principal ginseng saponins," *J. Nat. Prod.* (2003) 66: 922-927.
Beveridge et al., "Phytosterol content in American ginseng seed oil," *J. Agric. Food Chem.* (2002) 50: 744-750.
Office Action for Chinese Patent Application No. 200980122190.1 (Dec. 2, 2011).
Wang, "Progresses in studies on pharmacologic effects of ginsenosides," *Chinese Clinical Pharmacology and Therapeutics*, 11 (11): 1201-06 (Nov. 2006).

* cited by examiner

*Primary Examiner* — Lezah Roberts
*Assistant Examiner* — Nannette Holloman
(74) *Attorney, Agent, or Firm* — Merchant & Gould P.C.

(57) ABSTRACT

Provided are a use of a ginseng flower extract and a use of a ginseng seed extract. The ginseng seed extract includes ginseng seed oil or a ginseng seed residue extract. The uses include skin protection, anti-aging, anti-wrinkle, improvement of skin elasticity, skin whitening, skin moisturizing, prevention and improvement of skin dryness diseases such as atopy, removal of the horny layer, sebum control, anti-inflammation, prevention or improvement of skin troubles such as acne, improvement of skin complexion, prevention of hair loss, anti-dandruff, improvement of gloss and softness of hair, improvement of volume and elasticity of face or body, and improvement of facial or body line.

32 Claims, 4 Drawing Sheets

EXTERNAL PREPARATION COMPOSITION FOR SKIN COMPRISING GINSENG FLOWER OR GINSENG SEED EXTRACTS

CROSS-REFERENCE TO RELATED APPLICATION

This application is a National Stage Application of PCT/KR2009/002206, filed Mar. 28, 2009, which claims benefit of Korean Patent Application Nos. 10-2008-0055798 filed on Jun. 13, 2008, 10-2008-0056541 filed on Jun. 16, 2008, 10-2008-0124500 filed on Dec. 9, 2008, and 10-2008-0124479 filed Dec. 9, 2008 and all the benefits accruing therefrom under 35 U.S.C. §119, the contents of which in their entirety are herein incorporated by reference. To the extent appropriate, a claim of priority is made to each of the above disclosed applications.

BACKGROUND

1. Field

The present disclosure relates to a use of a ginseng flower extract and a use of a ginseng seed extract. The ginseng seed extract includes a ginseng seed oil extract or a ginseng seed residue extract. More particularly, the present disclosure relates to a use of the ginseng flower extract or the ginseng seed extract for skin protection, anti-aging, anti-wrinkle, improvement of skin elasticity, skin whitening, skin moisturizing, prevention and improvement of skin dryness diseases such as atopy, sebum control, anti-inflammation, prevention or improvement of skin troubles such as acne, removal of the horny layer, improvement of skin complexion, prevention of hair loss, anti-dandruff, improvement of gloss and softness of hair, improvement of volume and elasticity of face or body, or improvement of facial or body line.

2. Description of the Related Art

Ginseng (*Panax ginseng* C.A. Meyer) is a herbal plant belonging to the *Panax* genus in the family Araliaceae. It has been traditionally used for 2,000 years in Korea, China and Japan among other regions as a medicine to prevent diseases and prolong lives. Ginseng is known to have activities for the central nervous system, anticarcinogenic and anticancer activities, immune control activities, anti-diabetic activities, liver function enhancing effect, cardiovascular improving and antiarterioscleroic activities, blood pressure controlling activities, menopausal disorder and osteoporosis improving effects, anti-stress and fatigue-relieving effects, antioxidative activities, anti-aging effects, and the like.

Ginsenosides, the representative physiologically active compounds of ginseng, are distributed uniformly in the aerial part and the underground part of ginseng. However, the contents and compositions of ginsenosides are greatly different depending on the parts—i.e., root, leaves, fruits, etc. Especially, it is reported that the ginseng flower contains ginsenosides of different contents and compositions from the ginseng root, which provide superior liver protecting effects (*J. Nat. Prod.* 66; 922-927, 2003.). Since the ginseng seed has been used only to cultivate ginseng, little is known thereabout. For example, fatty acid compositions and phytosterol contents of ginseng seed are reported in *J. Agric. Food Chem.* 50, 744-750, 2002.

Recently, as the consumers' interest in natural products increases and a number of cosmetics based on herbal materials are released in the market, ginseng is also studied as an important source material of cosmetics. However, most of the studies are focused on ginseng root, specifically ginseng root extracts or ginsenosides and ginseng polysaccharide of the ginseng root. In contrast, ginseng flower or ginseng seed has not been studied at all.

SUMMARY

The present disclosure is directed to providing a preparation for external application for skin useful for the skin.

The present disclosure is also directed to providing a composition for protecting skin.

The present disclosure is also directed to providing a composition for protecting hair.

The present disclosure is also directed to providing a composition for preventing or improving aging.

The present disclosure is also directed to providing a composition for preventing or improving wrinkles.

The present disclosure is also directed to providing a composition for improving skin elasticity.

The present disclosure is also directed to providing a composition for skin whitening.

The present disclosure is also directed to providing a composition for skin moisturizing.

The present disclosure is also directed to providing a composition for preventing or improving skin dryness diseases such as atopy.

The present disclosure is also directed to providing a composition for removing the horny layer of the skin.

The present disclosure is also directed to providing a composition for controlling sebum of the skin.

The present disclosure is also directed to providing a composition for preventing or relieving inflammation.

The present disclosure is also directed to providing a composition for preventing or relieving inflammation of the scalp.

The present disclosure is also directed to providing a composition for preventing or improving skin troubles such as acne.

The present disclosure is also directed to providing a composition for preventing or improving skin troubles in the scalp such as acne.

The present disclosure is also directed to providing a composition for improving skin complexion.

The present disclosure is also directed to providing a composition for preventing hair loss.

The present disclosure is also directed to providing an anti-dandruff composition.

The present disclosure is also directed to providing a composition for improving gloss or softness of hair.

The present disclosure is also directed to providing a composition for improving volume and elasticity of face or body.

The present disclosure is also directed to providing a composition for improving facial or body line.

In one aspect, there is provided a composition for external application for skin including a ginseng flower extract or a ginseng seed extract as an effective ingredient.

In a composition for external application for skin according to an embodiment of the present disclosure, the ginseng seed extract may be ginseng seed oil. If the ginseng seed extract is ginseng seed oil, it may be included in an amount of 0.001 to 100 wt % based on the total weight of the composition for external application for skin.

In a composition for external application for skin according to another embodiment of the present disclosure, the ginseng seed extract may be a ginseng seed residue extract. The ginseng seed residue extract may be included in an amount of 0.001 to 10 wt % based on the total weight of the composition for external application for skin.

In an embodiment of the present disclosure, the composition for external application for skin may be used to protect skin by reducing skin damage. As used herein, the skin includes the scalp and hair. Thus, there is provided a composition for external application for skin for protecting hair by reducing scalp or hair damage.

In another embodiment of the present disclosure, the composition for external application for skin protects the skin by reducing skin damage caused by oxidation or UV. As used herein, the skin includes the scalp and hair. Thus, there is provided a composition for external application for skin for protecting the scalp or hair by reducing scalp or hair damage caused by oxidation or UV.

In another embodiment of the present disclosure, the composition for external application for skin is used to prevent or improve skin aging.

In another embodiment of the present disclosure, the composition for external application for skin suppresses skin aging through reduction of skin damage caused by oxidation or UV, promotion of collagen synthesis or inhibition of matrix metalloproteinase-1 (MMP-1) biosynthesis.

A composition for external application for skin according to another embodiment of the present disclosure is used to prevent or improve wrinkles.

A composition for external application for skin according to another embodiment of the present disclosure prevents or improves wrinkles through promotion of collagen synthesis or inhibition of MMP-1 biosynthesis.

A composition for external application for skin according to another embodiment of the present disclosure is used to improve skin elasticity.

A composition for external application for skin according to another embodiment of the present disclosure is used for skin whitening.

A composition for external application for skin according to another embodiment of the present disclosure performs skin whitening through inhibition of melanin synthesis or depigmentation of skin pigmentation.

A composition for external application for skin according to another embodiment of the present disclosure is used for skin moisturizing.

A composition for external application for skin according to another embodiment of the present disclosure keeps the skin moisturized through promotion of differentiation of keratinocytes or promotion of expression of transglutaminase.

A composition for external application for skin according to another embodiment of the present disclosure is used to prevent or improve skin dryness diseases including atopy or psoriasis.

In another embodiment of the present disclosure, the composition for external application for skin may be used to remove of the horny layer.

A composition for external application for skin according to another embodiment of the present disclosure is used to control skin sebum.

A composition for external application for skin according to another embodiment of the present disclosure controls the skin sebum by suppressing excretion of sebum.

A composition for external application for skin according to another embodiment of the present disclosure is used to prevent or improve inflammation or relieve irritation. As used herein, the skin includes the scalp. Thus, there is provided a composition for external application for skin for preventing or improving inflammation of the scalp and relieving irritation to the scalp.

A composition for external application for skin according to another embodiment of the present disclosure is used to prevent or improve skin troubles including acne. As used herein, the skin includes the scalp. Thus, there is provided a composition for external application for skin for preventing or improving skin troubles including acne on the scalp.

In another embodiment of the present disclosure, a composition for external application for skin is used to improve skin complexion.

In another embodiment of the present disclosure, composition for external application for skin is used to prevent hair loss.

In another embodiment of the present disclosure, a composition for external application for skin is used for anti-dandruff purpose.

In another embodiment of the present disclosure, a composition for external application for skin is used to improve gloss or softness of hair.

In another embodiment of the present disclosure, a composition for external application for skin is used to improve volume and elasticity of face or body.

In another embodiment of the present disclosure, a composition for external application for skin is used to improve facial or body line.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Exemplary embodiments now will be described more fully hereinafter with reference to the accompanying drawings, in which exemplary embodiments are shown. The present disclosure may, however, be embodied in many different forms and should not be construed as limited to the exemplary embodiments set forth therein. Rather, these exemplary embodiments are provided so that the present disclosure will be thorough and complete, and will fully convey the scope of the present disclosure to those skilled in the art. In the description, details of well-known features and techniques may be omitted to avoid unnecessarily obscuring the presented embodiments.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the term "extract" refers to any substance derived from a natural source, regardless of the particular method or ingredients. It includes, for example, one extracted from a natural source by dissolving with water or an organic solvent, or specific ingredients of the natural source such as oil.

As used herein, the term "ginseng seed oil" refers to oil derived from the seed of ginseng. For example, it may be an extract obtained from ginseng seed using an organic solvent such as hexane, ether, methylene chloride, or the like.

As used herein, the term "ginseng seed residue" refers to a residue remaining after removing oil from ginseng seed. For example, it may be a residue remaining after extracting oil from ginseng seed using an organic solvent such as hexane, ether, methylene chloride, or the like.

As used herein, the term "skin" refers to an outer covering of an animal. It is to be understood to include not only the face or body but also the scalp and hair.

In an embodiment of the present disclosure, the ginseng is *Panax ginseng* C.A. Meyer.

In an embodiment of the present disclosure, the ginseng flower extract may be included in an amount of 0.001 to 10 wt % based on the total weight of the composition for external application for skin, depending on the type of the composition, but without being limited thereto.

In another embodiment of the present disclosure, the ginseng flower extract may be prepared by adding water, a mixture of water and an organic solvent (ethanol, methanol, butanol, ether, ethyl acetate, chloroform, etc.) or an organic solvent to dried ginseng flower in an amount of 1 to 10 times (wt/v%) of the ginseng flower and keeping at room temperature for a day. Specifically, the extract may be obtained by repeating the above procedure twice. Also, specifically, after removing chlorophyll from the extract, the filtrate may be concentrated in a vacuum concentrator to obtain the ginseng flower extract in dry solid form.

In another embodiment of the present disclosure, the ginseng seed extract may be ginseng seed oil, and the oil may be included in an amount of 0.001 to 100 wt % based on the total weight of the composition for external application for skin, depending on the type of the composition. If the amount of the ginseng seed oil is less than 0.001 wt %, a desired effect may not be attained.

In another embodiment of the present disclosure, the ginseng seed oil may be obtained by crushing dried ginseng seed and extracting with an organic solvent (hexane, ether, methylene chloride, etc.) of 1 to 10 times (wt/v%) the amount of the crushed seed at room temperature for a day. For example, the extract may be obtained by repeating the above procedure 3 times. After filtering the extract, the filtrate may be concentrated in a vacuum concentrator to obtain the ginseng seed oil.

In a composition for external application for skin according to an embodiment of the present disclosure, the ginseng seed residue extract may be included in an amount of 0.001 to 10 wt % based on the total weight of the composition for external application for skin, depending on the type of the composition. If the amount of the ginseng seed residue extract is less than 0.001 wt %, a desired effect may not be attained. And, even if the amount exceeds 10 wt %, the effect does not increase in proportion to the addition amount.

The ginseng seed residue extract may be prepared as follows. Dried ginseng seed is crushed and extracted in 1 to 10 times (wt/v %) the amount of an organic solvent such as hexane at room temperature for a day. After repeating this procedure 3 times to remove oil from the ginseng seed, the remaining ginseng seed residue is extracted in 1 to 10 times (wt/v %) the amount of water, a mixture of water and an organic solvent (ethanol, methanol, butanol, ether, ethyl acetate, chloroform, etc.) or an organic solvent at room temperature for a day. This procedure is repeated 3 times. The resulting extract is filtered, and the filtrate is concentrated in a vacuum concentrator to obtain the ginseng seed residue extract in dry solid form.

Human skin undergoes changes as it ages due to various internal and external factors. Internally, the secretion of metabolism-regulating hormones decreases and the function of immune cells and the activity of cells are reduced, thus resulting in decreased biosynthesis of immunoproteins and other proteins. Externally, increased free radicals and reactive oxygen species resulting from the increased UV radiation due to the depletion of the ozone layer and the increased environmental pollution leads to reduced skin thickness, increased wrinkles, decreased elasticity, poor skin complexion, frequent skin troubles, increased liver spots, freckles and age spots, among others.

With the progression of skin aging, the content and arrangement of skin components, such as collagen, elastin, hyaluronic acid and glycoprotein, change or decrease, and the skin undergoes oxidative stress by free radicals and reactive oxygen species. It is known that, with the progression of aging or by UV light, the biosynthesis of cyclooxygenase-2 (Cox-2), which produces proinflammatory cytokines known to cause inflammation, increases, the biosynthesis of matrix metalloproteinase (MMP), which degrades the skin tissue due to these inflammatory factors, increases, and the production of nitric oxide (NO) by inducible nitric oxide synthase (iNOS) increases in most cells constituting the skin. That is, the biosynthesis of matrix materials is reduced due to a decrease in cell activity, resulting from intrinsic aging, which naturally progresses, and microinflammation, and degradation and degeneration are accelerated due to extrinsic factors, such as stresses resulting from various harmful environments and increase in reactive oxygen species, so that the skin matrix is destroyed and becomes thin, while various skin aging symptoms appear.

Since the disclosed composition for external application for skin contains a ginseng flower extract or a ginseng seed extract, which are effective in suppressing the generation of reactive oxygen species and reducing oxidative damage induced by the reactive oxygen species, as an effective ingredient, it is capable of preventing cell damage caused by the reactive oxygen species or UV and thus protecting the skin. Further, it can suppress the progression of aging caused by the reactive oxygen species or UV. Further, the ginseng flower extract or the ginseng seed extract can improve prevent or improve inflammation by suppressing the biosynthesis of COX-2 and thus relieving skin troubles. Here, the skin includes the scalp. That is, the disclosed ginseng flower extract or ginseng seed extract may be used to prevent damage to the scalp or hair caused by the reactive oxygen species or UV, prevent or improve inflammation of the scalp, and relieve irritation to the scalp caused by hair perm or hair dyeing. In addition, the disclosed ginseng flower extract or ginseng seed extract may be used to prevent or improve skin wrinkles.

Various factors are involved in determining the human skin color. Among them, the activity of melanocytes producing melanin pigments, the distribution of blood vessels, the thickness of the skin, and the presence or absence of pigments such as carotenoids and bilirubin in the human body, are important.

The most important factor among them is the black pigment melanin which is produced by the action of various enzymes such as tyrosinase in melanocytes. The production of the melanin pigment is influenced by genetic factors, physiological factors associated with hormone secretion and stress, and environmental factors such as UV radiation.

The melanin pigment, which is produced by melanocytes, is a phenolic polymer in the form of a black pigment/protein composite and has useful functions to protect skin organs under the dermis by blocking UV light radiation from the sun and simultaneously to capture free radicals from the skin, thus protecting proteins and genes in the skin.

Melanin produced in the skin due to intrinsic and extrinsic stresses as described above is a stable material and does not disappear until it is discharged to the outside through skin keratinization, even when the stresses disappear. However, if melanin is produced larger than required, hyperpigmentation such as freckles and spots is induced, leading to unfavorable results in the sense of beauty.

The disclosed ginseng flower extract or ginseng seed extract is capable of whitening the skin by suppressing the production of melanin. Thus, the disclosed composition for external application for skin comprising the ginseng flower extract or ginseng seed extract as an effective ingredient may be used for skin whitening.

The most important function of the epidermis, which is the outermost layer of the skin, is to protect the skin from various external stimuli (physical and chemical stimuli such as chemicals, pollutants, dry environment and UV radiation) and to prevent excessive loss of water through the skin. This protective function can be maintained only when the horny layer consisting of keratinocytes are formed normally. The horny layer (stratum corneum), the outermost layer of the epidermis, is formed from keratinocytes and consists of terminally differentiated keratinocytes surrounded by lipid layers. Keratinocytes are the cells generated as a result of the process in which basal cells that continuously proliferate in the lowest layer of the epidermis move up toward the skin's surface while they undergo a series of structural and functional changes. After a given period, old keratinocytes are shed from the skin and replaced by new keratinocytes. This repeated process is called "differentiation of epidermal cells" or "keratinization". During the keratinization process, keratinocytes form the horny layer, while they produce natural moisturizing factors (NMFs) and intercellular lipids (ceramides, cholesterols and fatty acids), such that the horny layer has firmness and softness to function as a skin barrier.

However, this horny layer can easily lose its functions due to lifestyle factors such as excessive face washing or bathing, environmental factors such as dry atmosphere or pollutants, and intrinsic diseases such as atopy or geriatric skin disease. In fact, due to various factors which have increased recently, more and more people are suffering from dry skin symptoms and various disorders. Thus, in order to keep the skin moisturized at a suitable level, many studies focused on supplying water from outside or preventing loss of water from the body have been conducted. In fact, various kinds of moisturizers having water retention capability have been developed and used mainly in the cosmetic field.

However, as harmful factors to the human body gradually increase in the living environment and an aged population increases rapidly, the turnover rate of the horny layer becomes slower, and the lipid synthesis capability of keratinocytes is reduced, or the division, growth and differentiation of cells in the epidermis become inefficient. As a result, more people have such skin conditions that the quantity of moisturizing factors and lipids is insufficient and the function of the horny layer is not maintained (i.e., the skin barrier function is not maintained).

The abnormality in the division and differentiation of epidermal cells causes various skin diseases, including xeroderma, atopy and psoriasis. Such diseases can be slightly relieved with existing moisturizers having water retention capability only, but it is difficult to expect fundamental cure of the diseases.

The disclosed ginseng flower extract or ginseng seed extract aids in the "differentiation of epidermal cells" or "keratinization" by facilitating the differentiation of keratinocytes and thus is capable of effectively removing the horny layer. The disclosed composition for external application for skin, which comprises the ginseng flower extract or the ginseng seed extract having superior removal effect of the horny layer as an effective ingredient, may be used as for removal of the horny layer.

Further, the disclosed ginseng flower extract or ginseng seed extract helps to maintain the quantity of moisturizing factors and lipids in the horny layer at normal levels by maintaining the turnover rate of the horny layer. In addition, it facilitates the expression of transglutaminase, thereby keeping the skin moisturized.

Further, the disclosed ginseng flower extract or ginseng seed extract may enhance the skin barrier function by facilitating the differentiation of keratinocytes and keeping the skin moisturized, and thus may be used to prevent or treat skin dryness diseases such as atopy or psoriasis.

In the skin including the scalp and face, sebum generally functions to keep the skin moisturized or prevent the invasion of microorganisms. However, if sebum is secreted excessively, hair loss is accelerated, acne worsens, resulting in enlargement of follicles, and seborrheic dermatitis occurs.

The excessive sebum secretion is caused by various factors. The most important factor is the stimulation of sebaceous gland cells by dihydrotestosterone (DHT), which is one of the hormones involved in promotion of sebum secretion. In hair, testosterone is converted into DHT by 5-α-reductase type 2 in cells and, at the same time, binds to a receptor in the cytoplasm and enters the nucleus, thus causing loss of hair. In contrast, in the skin or the sebaceous glands, testosterone is converted into DHT by 5-α-reductase type 1 to activate sebaceous gland cells and to stimulate the differentiation of the cells, and thus serum in is secreted excessively the sebaceous glands, thus causing acne.

In addition to the simple excessive secretion of sebum, skin troubles such as acne and hair loss are aggravated by microinflammations of the skin. Excessive accumulation of sebum in hair follicles activates the acne germ (*Propionibacterium acnes*) and causes inflammation.

By suppressing sebum excretion, the disclosed ginseng flower extract or ginseng seed extract may prevent or improve acne, enlargement of follicles, seborrheic dermatitis, or the like caused by excessive sebum secretion.

The disclosed composition for external application for skin may improve volume and elasticity of face or body by promoting the differentiation of adipocytes. It can be achieved by applying the disclosed composition for external application for skin on the part of face or body where the improvement of volume and elasticity is desired. The part where the improvement of volume and elasticity is desired may be, for example, the part where depression has occurred due to aging. By applying the composition for external application for skin on the depressed cheeks, volume may be improved through facilitated differentiation of adipocytes. As another example, the part where the improvement of volume and elasticity is desired may be the breast and hip. By applying the composition for external application for skin on the breast and hip, the breast and hip may be made more elastic and voluptuous.

The disclosed composition for external application for skin may also be used to improve facial or body line. As well as improving volume and elasticity of the face and body by promoting differentiation of adipocytes, the ginseng flower extract or the ginseng seed extract included as the effective ingredient may improve the facial or body line impaired by aging or the like by promoting collagen biosynthesis and suppressing collagen degradation.

A cosmetic composition for external application for skin according to the present disclosure contains a cosmetically or dermatologically acceptable medium or base. It may be provided in the form of all formulations suitable for topical application, for example, solutions, gels, solids, pastes, emulsions obtained by dispersing an oily phase in an aqueous phase, suspensions, microemulsions, microcapsules or microgranules, ionic (liposomal) and non-ionic dispersions, creams, toner, lotions, powder, ointments, sprays or concealer sticks. These compositions may be prepared according to any method known in the art. The composition according to the present disclosure may also be used in the form of foam or an aerosol composition further containing a compressed propellant.

The cosmetic composition of the present disclosure may contain additives, which are commonly used in the cosmetic or dermatological field, including fatty materials, organic solvents, solubilizing agents, concentrating agents, gelling agents, softening agents, antioxidants, suspending agents, stabilizing agents, foaming agents, aromatic agents, surfactants, water, ionic or non-ionic emulsifiers, fillers, sequestering agents, chelating agents, preservatives, vitamins, blocking agents, wetting agents, essential oil, dyes, pigments, hydrophilic or lipophilic activators, lipid vesicles, or other components which are commonly used in cosmetic products. The additives are introduced in an amount which is generally used in the cosmetic or dermatological field.

There is no particular limitation on the formulation of composition for external application for skin comprising the ginseng flower extract or ginseng seed extract of the present disclosure. It may be formulated into cosmetic products, for example, skin lotion, astringent lotion, milk lotion, nourishing cream, massage cream, essence, eye cream, eye essence, cleansing cream, cleansing foam, cleansing water, pack, powder, body lotion, body cream, body oil and body essence.

The composition for external application for skin according to the present disclosure may be a pharmaceutical composition. The pharmaceutical composition may contain pharmaceutical additives such as antiseptics, stabilizing agents, hydrating agents, emulsification promoters or salts and/or buffers for osmotic control and may further contain other therapeutically useful materials. The pharmaceutical composition may be formulated into lotion, cream, ointment, gel, or the like.

The pharmaceutical composition may be administered transdermally.

The administration dose of the ginseng flower extract or the ginseng seed extract included in the pharmaceutical composition as the effective ingredient may vary depending on the age, sex and body weight of the patient in need of treatment, the particular disease to be treated or pathological conditions thereof, severity of the disease or pathological conditions, administration route, and discretion of a physician or pharmacist. The administration dose may be determined by those skilled in the art in consideration of those factors. A general administration dose is about 0.0001 mg/kg/day to about 2000 g/kg/day.

EXAMPLES

The examples and experiments will now be described. The following examples and experiments are for illustrative purposes only and not intended to limit the scope of the present disclosure.

Example 1

Preparation of Ginseng Flower Extract

Dried ginseng flower (1 kg) was added to 70% (v/v) ethanol (10 L) and extracted by keeping at room temperature for a day. The procedure was repeated twice. The resulting extract was filtered and the filtrate was concentrated to 2 L in a vacuum concentrator. Then, after adding ether of the same volume, the ether layer was removed from the filtrate to remove chlorophyll. This procedure was repeated 3 times. Then, the remaining extract was concentrated in a vacuum concentrator. Dry solid (150 g) was yielded.

Example 2

Preparation of Ginseng Seed Oil

Dried ginseng seed (1 kg) was crushed and, after adding hexane (10 L), extracted by keeping at room temperature for a day. The procedure was repeated 3 times. The resulting extract was filtered and the filtrate was concentrated in a vacuum concentrator. Ginseng seed oil (120 g) was yielded. After adding sodium hydroxide to the resulting extract oil to remove free fatty acid and washing 3 times with distilled water, decolorization using carbon and removal of foul-smelling components at 100° C. in vacuum using inert gas yielded ginseng seed oil (100 g).

Example 3

Preparation of Ginseng Seed Residue Extract

Dried ginseng seed (1 kg) was crushed and, after adding hexane (10 L), extracted by keeping at room temperature for a day. The procedure was repeated 3 times to remove oil from the ginseng seed. The remaining ginseng seed residue was extracted in water (10 L) by keeping at room temperature for a day. This procedure was repeated 3 times. The resulting extract was filtered and the filtrate was concentrated in a vacuum concentrator. Dry solid (100 g) was yielded.

Test Example 1

Inhibition of Reactive Oxygen Species Production

Antioxidative effect of the ginseng flower extract and the ginseng seed extract was investigated by comparing the capacity of removing reactive oxygen species (ROS) produced in cells in response to UV radiation.

Figure 1:
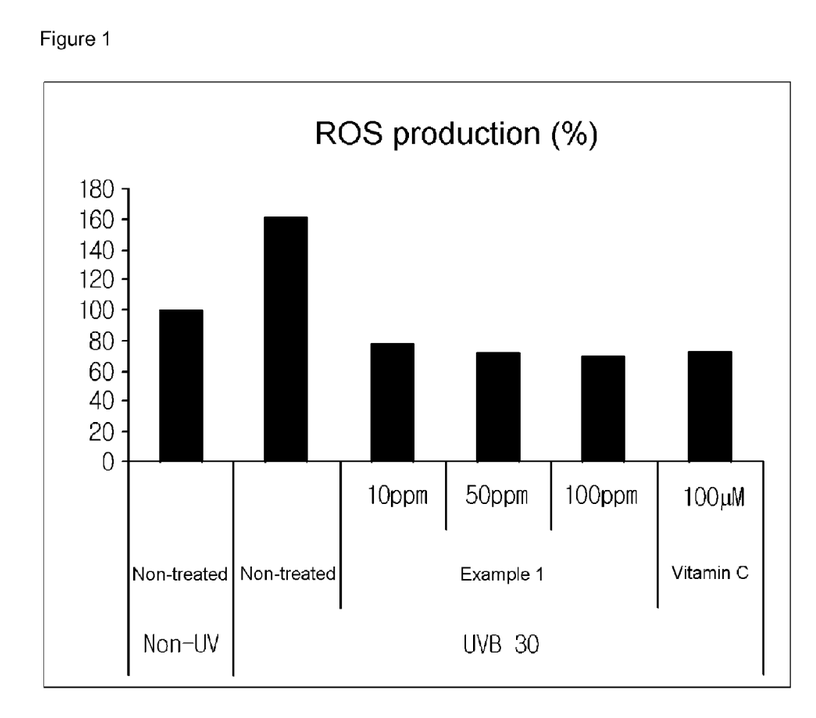
FIG. 1 is a graph showing the ability of suppressing generation of reactive oxygen species (ROS) of a ginseng flower extract according an embodiment of the present disclosure.

The positive control group for the ginseng flower extract was treated with vitamin C (Sigma Co.), which is commonly used to compare antioxidative effect. And, the control group was left untreated. A human HaCaT keratinocyte monolayer culture system (P. Boukamp, German Cancer Research Center, Heidelberg, Germany) was treated with UV (UVB 30 mJ/cm$^2$) and then with the extract prepared in Example 1 at 10 ppm, 50 ppm and 100 ppm. Then, 2',7'-dichlorodihydrofluorescein diacetate (DCFH-DA; Molecular Probes, Inc.) was measured with a fluorescence plate reader. Production of ROS was calculated relative to the UV-untreated control group. The result is shown in Table 1 and FIG. 1.

TABLE 1

| Treatment | ROS production (%) |
| --- | --- |
| Non-UVB | 100 |
| UVB | 161 |
| UVB + Example 1 (10 ppm) | 78 |
| UVB + Example 1 (50 ppm) | 72 |
| UVB + Example 1 (100 ppm) | 70 |
| UVB + vitamin C (100 µM) | 72 |

The positive control group for the ginseng seed extract was treated with Trolox (Aldrich Co.), which is commonly used to compare antioxidative effect. And, the control group was left untreated. A human HaCaT keratinocyte monolayer culture system (P. Boukamp, German Cancer Research Center, Heidelberg, Germany) was treated with UV (UVB 30 mJ/cm$^2$) and then with the ginseng seed oil prepared in Example 2 and the ginseng seed residue extract prepared in Example 3 as seen in Table 2. Then, DCFH-DA (Molecular Probes, Inc.) was measured with a fluorescence plate reader. Inhibition of ROS production was calculated relative to the UV-treated control group. The result is shown in Table 2.

TABLE 2

| Treatment | Inhibition of ROS production (%) |
| --- | --- |
| Control | 0 |
| Trolox (0.1 mM) | 42.7 |
| Example 2 (10 ppm) | 52.9 |
| Example 2 (1 ppm) | 38.3 |
| Example 3 (10 ppm) | 58.1 |
| Example 3 (1 ppm) | 45.9 |

The ginseng flower extract prepared in Example 1, the ginseng seed oil prepared in Example 2 and the ginseng seed residue extract prepared in Example 3 exhibited significant effect of removing UV-induced ROS in the human HaCaT keratinocyte monolayer culture system as compared to the control group. They showed superior antioxidant activities comparable to that of vitamin C or Trolox. That is to say, it was confirmed that, by effectively removing ROS which are causative of skin damage, the ginseng flower extract prepared in Example 1, the ginseng seed oil prepared in Example 2 and the ginseng seed residue extract prepared in Example 3 according to the present disclosure can protect the skin including the scalp and hair and prevent wrinkle formation, decrease of skin elasticity, pigmentation, or the like.

Test Example 2

Evaluation of Activity of Inhibiting Oxidative Damage of DNA By Single Cell Gel Electrophoresis (SCGE; Comet Assay)

Figure 2:
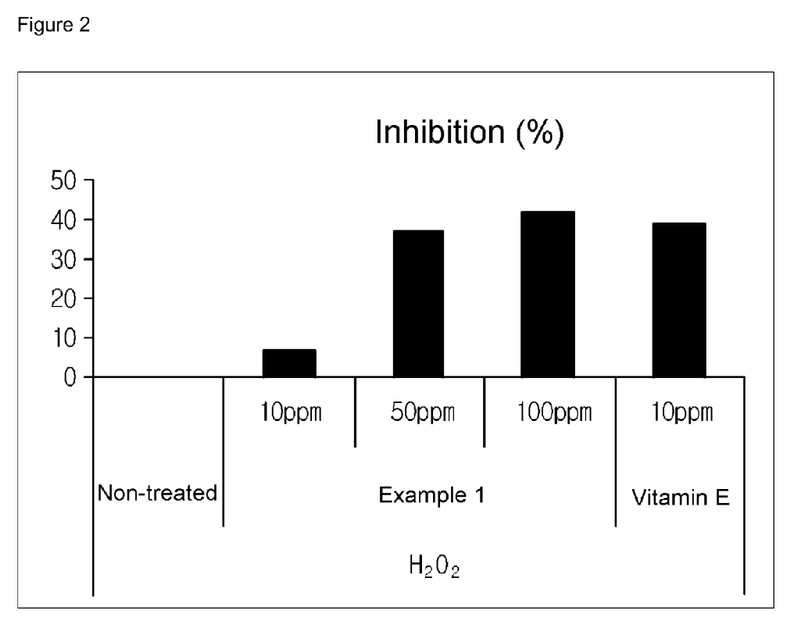
FIG. 2 is a graph showing the activity of suppressing oxidative damage to DNA of a ginseng flower extract according an embodiment of the present disclosure.

Human normal fibroblasts were cultured for 24 hours and treated with varying concentrations of the ginseng flower extract prepared in Example 1, the ginseng seed oil prepared in Example 2, the ginseng seed residue extract prepared in Example 3 and vitamin E. After 12 hours, the cells were treated with the positive control H$_2$O$_2$ (final concentration: 10$^{-3}$ M), stained by electrophoresis, and then observed with a fluorescence microscope. The image analyzer Komet 3.1 (Kinetic Imaging, England) was used to analyze the tail length (µm) resulting from the digestion of DNA in each of 25 cells. The result is shown in Table 3 and FIG. 2.

TABLE 3

| Treatment | Concentration | Tail length (µm) | Inhibition (%) |
| --- | --- | --- | --- |
| Control | None | 112.4 | — |
| Vitamin E | 10 ppm | 68.9 | 38.7 |
| Example 1 | 10 ppm | 104.6 | 6.9 |
|  | 50 ppm | 70.2 | 37.5 |
|  | 100 ppm | 65.4 | 41.8 |
| Example 2 | 1 ppm | 70.7 | 37.1 |
|  | 10 ppm | 39.1 | 43.2 |
| Example 3 | 1 ppm | 76.5 | 26.9 |
|  | 10 ppm | 42.3 | 39.8 |

As seen from Table 3, the cell gel electrophoresis showed that the ginseng flower extract prepared in Example 1, the ginseng seed oil prepared in Example 2 and the ginseng seed residue extract prepared in Example 3 had significant inhibitory activity against oxidative damage to DNA, suggesting that the ginseng flower extract or the ginseng seed extract according to the present disclosure can act as an inhibitor of oxidative DNA damage, which inhibits single-strand break of DNA caused by a hydroxyl radical (.OH). This provides an important defensive effect of protecting the genes of skin cells, including the scalp or hair.

Test Example 3

Analysis of Procollagen I Synthesis (Type I Procollagen Assay)

Figure 3:
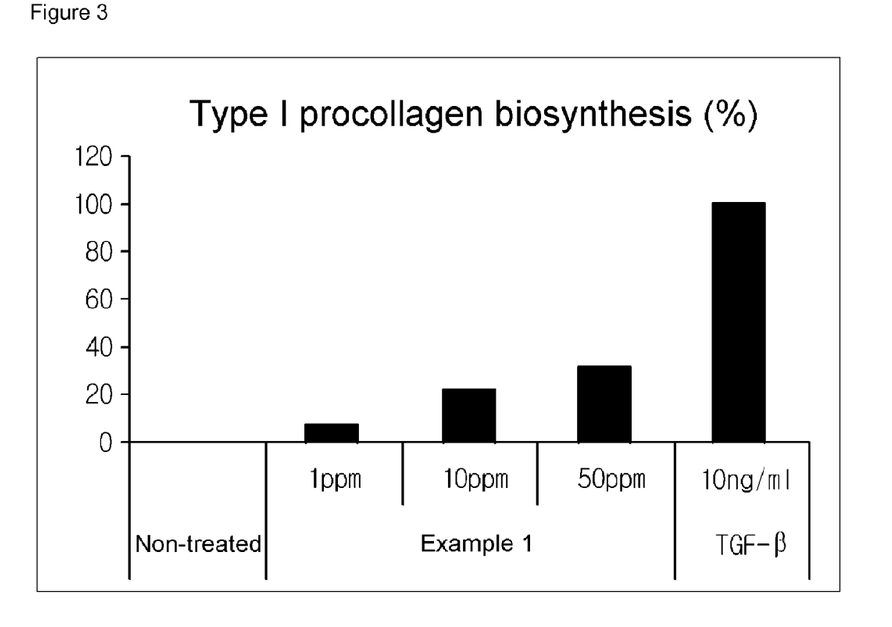
FIG. 3 is a graph showing the effect of a ginseng flower extract according an embodiment of the present disclosure on the synthesis of procollagen I.

Human fibroblasts were cultured in a 12-well culture plate at a concentration of 10$^5$ cells/well, and then the medium was replaced with media containing 1 ppm, 10 ppm and 50 ppm of the ginseng flower extract prepared in Example 1 or with media containing 1 ppm and 10 ppm of the ginseng seed oil prepared in Example 2 or the ginseng seed residue extract prepared in Example 3, as shown in Table 4. At 3 days of culture, the cells were harvested, and the amount of the produced type I procollagen was quantified using an ELISA method. The measurement results were calculated relative to 0 for the control group containing neither the ginseng flower extract nor the ginseng seed extract and 100 for the positive control group (human transforming growth factor-β1 (TGF-β1, Roche Co.)). The result is shown in Table 4 and FIG. 3.

TABLE 4

|  | Type I procollagen biosynthesis (%) |
| --- | --- |
| Negative control | 0 |
| Example 1 (1 ppm) | 7 |
| Example 2 (1 ppm) | 19 |
| Example 3 (1 ppm) | 11 |
| Example 1 (10 ppm) | 22 |
| Example 2 (10 ppm) | 39 |
| Example 3 (10 ppm) | 25 |
| Example 1 (50 ppm) | 31 |
| TGF-β1 (10 ng/mL) | 100 |

In the normal human fibroblast monolayer culture system, the ginseng flower extract prepared in Example 1, the ginseng seed oil prepared in Example 2 and the ginseng seed residue extract prepared in Example 3 showed the effect of significantly promoting the production of type I procollagen compared to the control group. That is to say, the composition for external application for skin including the ginseng flower extract or the ginseng seed extract according to the present disclosure could inhibit a decrease in collagen production resulting from human skin aging by promoting collagen synthesis.

Test Example 4

Analysis of Inhibition of MMP-1 Expression

Figure 4:
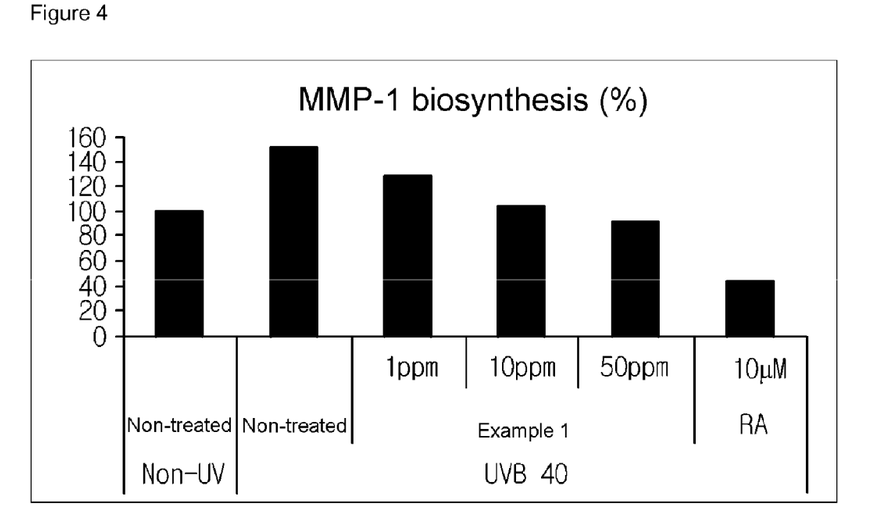
FIG. 4 is a graph showing the effect of a ginseng flower extract according an embodiment of the present disclosure on the expression of metalloproteinase-1 (MMP-1)

Human fibroblasts were cultured in a 12-well culture plate at a concentration of $10^5$ cells/well, and then irradiated with 40 mJ/cm$^2$ of UVB. Then, the culture medium was replaced with media containing 1 ppm, 10 ppm and 50 ppm of the ginseng flower extract prepared in Example 1. At 2 days of culture, the cells were harvested, and the amount of produced matrix metalloproteinase 1 (MMP-1) was quantified using an ELISA method. The measurement results were calculated relative to 100 for the non-UV-irradiated control group not treated with the test material. The positive control group was treated with retinoic acid (RA, Sigma Co.). The result is shown in Table 5 and FIG. 4.

TABLE 5

|  | MMP-1 biosynthesis (%) |
| --- | --- |
| Non-UV | 100 |
| UV | 152 |
| UV + Example 1 (1 ppm) | 128 |
| UV + Example 1 (10 ppm) | 105 |
| UV + Example 1 (50 ppm) | 92 |
| UV + RA (10 μM) | 45 |

In the normal human fibroblast monolayer culture system, the ginseng flower extract prepared in Example 1 according the present disclosure significantly inhibited the expression of MMP-1 induced by 40 mJ/cm$^2$ of UVB. This suggests that the ginseng flower extract prepared in Example 1 according the present disclosure has effects on the inhibition of skin aging and the reduction of wrinkles by inhibiting the biosynthesis of the skin tissue degrading enzyme MMP-1 resulting from intrinsic aging or external environmental factors.

Test Example 5

Effect of Improving Human Skin Wrinkles

A nourishing cream containing the ginseng flower extract prepared in Example 1 (Example 4), a nourishing cream containing the ginseng seed oil prepared in Example 2 and the ginseng seed residue extract prepared in Example 3 (Example 5), and a nourishing cream containing neither the ginseng flower extract nor the ginseng seed extract (Comparative Example 1) were prepared as shown in Table 6. The prepared creams were applied to 120 test subjects aged between 30 and 50 and having facial wrinkles. The effects of the creams on the improvement of skin wrinkles were compared (unit: wt %).

TABLE 6

| Components | Example 4 | Example 5 | Comparative Example 1 |
| --- | --- | --- | --- |
| Ginseng flower extract | 0.1 | — | — |
| Ginseng seed oil | — | 0.1 | — |
| Ginseng seed residue extract | — | 0.1 | — |
| Beeswax | 10 | 10 | 10 |
| Polysorbate 60 | 1.5 | 1.5 | 1.5 |
| PEG 60 hydrogenated castor oil | 2 | 2 | 2 |
| Sorbitan sesquioleate | 0.5 | 0.5 | 0.5 |
| Liquid paraffin | 10 | 10 | 10 |
| Squalane | 5 | 5 | 5 |
| Capylic/capric triglyceride (Estasan: Uniqema) | 5 | 5 | 5 |
| Glycerin | 5 | 5 | 5 |
| Butylene glycol | 3 | 3 | 3 |
| Propylene glycol | 3 | 3 | 3 |
| Triethanolamine | 0.2 | 0.2 | 0.2 |
| Preservative, pigment and fragrance | qs | qs | qs |
| Purified water | balance | balance | balance |

The nourishing cream of Example 4 or 5 was applied on the left side of the face of the subjects for 3 months, and the nourishing cream of Comparative Example 1 was applied on the right side for 3 months. The conditions of both sides of the face were measured before application of the creams, and after 3-month application of the creams, the conditions of the same portions were measured again, thus measuring changes in skin wrinkles. In a constant-temperature and constant-humidity chamber at a temperature of 24° C. and a relative humidity of 40%, wrinkles at the outer corner of the eyes were reproduced with a replica, and the wrinkles were measured with a visiometer system (C+K Inc.). The change in skin wrinkles was calculated according to Equation 1.

$$\text{Change } (\Delta\%) = [(Tdi - Tdo)/Tdo] \times 100 \qquad \text{[Equation 1]}$$

In Equation 1, "Tdi" is a value measured at D90, and "Tdo" is a value measured at D0.

In the results of calculation according to Equation 1, whereas the skin wrinkles at the portion applied with the nourishing cream of Comparative Example 1 showed a decrease of 6.1±7% (mean ±standard deviation), the skin wrinkles at the portion applied with the nourishing creams of Example 4 and 5 showed a decrease of 35±8% and 32±5%, respectively, suggesting an excellent effect of improving skin wrinkles.

Test Example 6

Effect of Improving Skin Elasticity in Human

Skin elasticity improvement effects of the creams prepared in Examples 4 and 5 and Comparative Example 1 were measured. Sixty (60) women aged 30 years or older were divided into 3 groups. The faces of the subjects in each of the groups were applied with the nourishing creams of Examples 4 and 5 Comparative Example 1 two times every day for 12 weeks, and then the skin elasticity of the faces was measured using a skin elasticity measuring instrument (Cutometer SEM 575, C+K Electronic Co., Germany). As a result, whereas the cream of Comparative Example 1 showed a skin viscoelasticity measured with the skin elasticity measuring instrument of 0.21±0.14 (mean ±standard deviation), the creams of Examples 4 and 5 resulted in a skin viscoelasticity of 0.30±0.10 and 0.29±0.08, respectively, suggesting superior improvement of skin elasticity.

That is to say, use of the nourishing cream of Example 4 containing the ginseng flower extract prepared in Example 1 showed a skin elasticity improvement effect of about 140%.

Test Example 7

Analysis of Melanin Synthesis Inhibition Effect Using Mouse Melanocytes

Mouse melanocytes were used to examine the melanin synthesis inhibitory effect of the ginseng flower extract prepared in Example 1, the ginseng seed oil prepared in Example 2 and the ginseng seed residue extract prepared in Example 3. First, C57BL/6 mouse melanocytes (Mel-Ab cells; Dooley, T. P. et al., *Skin Pharmacol.*, 7, pp. 188-200) were cultured in Dulbecco's modified Eagle's medium (DMEM) containing 10% fetal bovine serum, 100 nM 2-O-tetradecanoylphorbol-13-acetate and 1 nM cholera toxin under the condition of 37° C. and 5% $CO_2$. The cultured Mel-Ab cells were detached with 0.25% trypsin-EDTA and cultured in a 24-well culture plate at a concentration of $10^5$ cells/well. Then, from day 2 of culture, each of 10 ppm, 50 ppm and 100 ppm of the ginseng flower extract (Example 1), the ginseng seed oil (Example 2) and the ginseng seed residue extract (Example 3) was continuously added thereto and cultured for 3 days. The positive control group was treated with arbutin (Sigma Co.). Then, the culture media were removed, and the cells were washed with PBS and lysed with 1 N sodium hydroxide. The lysed cells were measured for absorbance at 400 nm, and then the inhibition of melanin production was calculated according to Equation 2. The result is shown in Table 7, FIG. 5 and FIG. 6 (Dooley's method).

Figure 5:
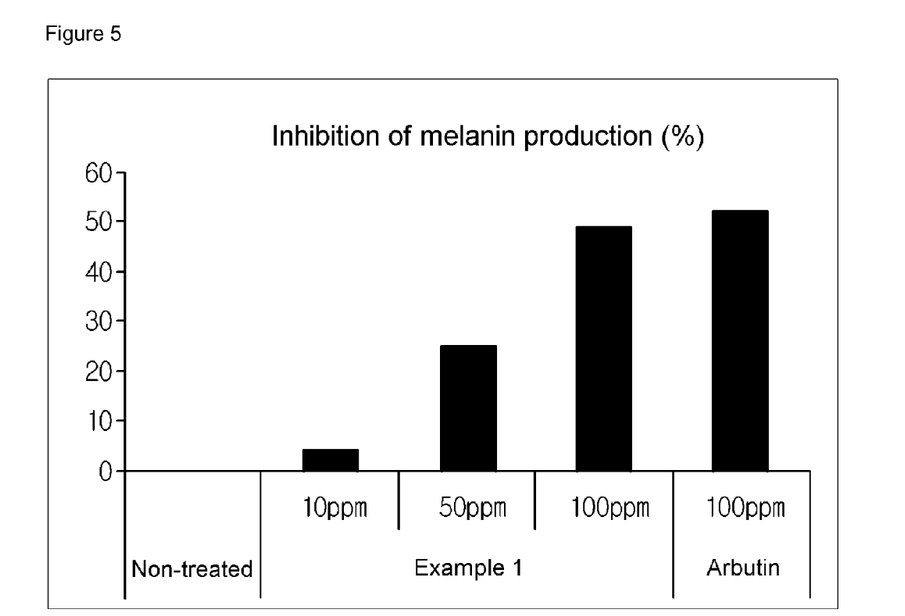
FIG. 5 is a graph showing the effect of a ginseng flower extract according an embodiment of the present disclosure on melanin synthesis.
Figure 6:
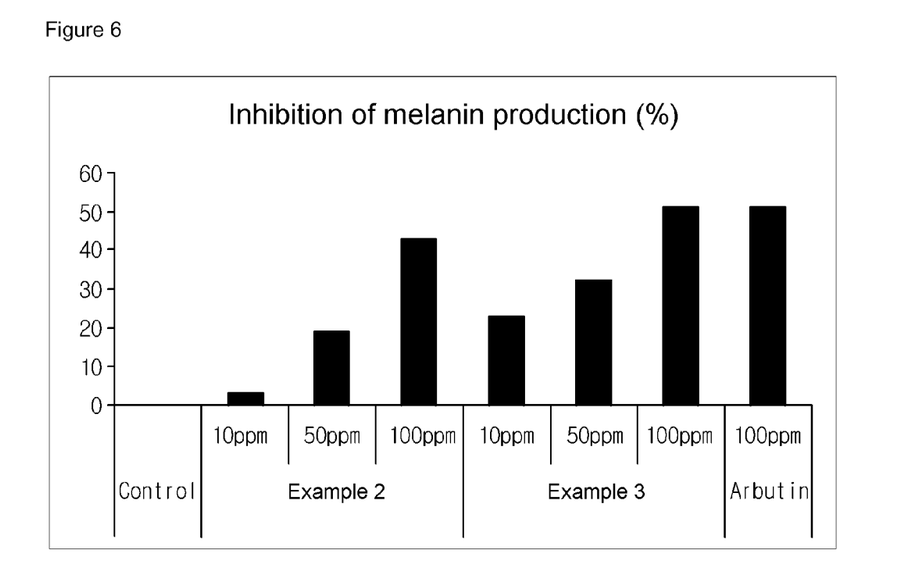
FIG. 6 is a graph showing the effect of a ginseng seed extract according an embodiment of the present disclosure on the inhibition of melanin synthesis.

Melanin synthesis inhibition (%)=100−[(Absorbance of each test material/Absorbance of control)× 100]  [Equation 2]

TABLE 7

| Melanin synthesis inhibition (%) | Example 1 | Example 2 | Example 3 |
|---|---|---|---|
| Non-treated | 0 | 0 | 0 |
| 10 ppm | 4 | 3 | 23 |
| 50 ppm | 25 | 19 | 32 |
| 100 ppm | 49 | 43 | 51 |
| Arbutin 100 ppm | | 51 | |

As shown in Table 7, it was found that the ginseng flower extract prepared in Example 1, the ginseng seed oil prepared in Example 2 and the ginseng seed residue extract prepared in Example 3 according to the present disclosure showed melanin synthesis inhibition rates comparable to that of arbutin. This means that the ginseng flower extract prepared in Example 1, the ginseng seed oil prepared in Example 2 and the ginseng seed residue extract prepared in Example 3 according to the present disclosure may exhibit excellent whitening effect.

Test Example 8

Whitening on Human Skin

In order to examine the whitening effect of the ginseng flower extract prepared in Example 1, the ginseng seed oil prepared in Example 2 and the ginseng seed residue extract prepared in Example 3 on human skin, the following test was carried out.

First, for 12 healthy men, a 1.5-cm perforated opaque tape was attached to the upper arm portion of the subjects, and then the attached portion was irradiated with UVB at a dose of about 1.5-2 times the minimal erythemal dose of each subject to induce skin darkening.

After the UV radiation, each of the ginseng flower extract prepared in Example 1, the ginseng seed oil prepared in Example 2 and the ginseng seed residue extract prepared in Example 3 and hydroquinone was applied on the UV-irradiated portion, and a change in the state of the applied portion was observed for 10 weeks in comparison with the control portion with anything applied thereon. The color of the skin was measured with the colorimeter CR2002 (Minolta, Japan) at 1-week intervals.

Then, the difference in skin color ($\Delta L^*$) between the time point of initiation of application and the time point of completion of application of each test material was calculated according to Equation 3, and the calculation results are shown in Table 8. The whitening effect is evaluated by measuring the $\Delta L^*$ value between the sample-applied portion and the control portion. A $\Delta L^*$ value of about 2 indicates that the skin whitening is distinct, and if it is more than about 1.5, it can be judged that there exists a whitening effect.

$L^*=L^*$ value at the time of completion of application−
$L^*$ value at the time of initiation of application  [Equation 3]

TABLE 8

| Test materials | Skin color brightness ($\Delta L^*$) |
|---|---|
| Example 1 | 1.91 ± 0.17 |
| Example 2 | 1.94 ± 0.11 |
| Example 3 | 1.91 ± 0.14 |
| Hydroquinone (positive control) | 1.89 ± 0.15 |
| Vehicle (negative control) | 0.51 ± 0.13 |

As shown in Table 8, the ginseng flower extract prepared in Example 1, the ginseng seed oil prepared in Example 2 and the ginseng seed residue extract prepared in Example 3 according to the present disclosure showed skin color brightness similar to that of hydroquinone. This is because the ginseng flower extract, the ginseng seed oil and the ginseng seed residue extract improve pigmentation resulting from UV radiation and make the skin color brighter.

Test Example 9

Induction of Differentiation of Human Keratinocytes

The effect of the ginseng flower extract prepared in Example 1, the ginseng seed oil prepared in Example 2 and the ginseng seed residue extract prepared in Example 3 according to the present disclosure on the promotion of cell differentiation was examined by measuring the amount of cornified envelope (CE) produced during the differentiation of keratinocytes and the human keratinocyte cell line (HaCaT).

Primarily cultured human keratinocytes were placed in a culture flask and allowed to adhere to the bottom of the flask, and then the test materials shown in Table 9 were added to the culture media at varying concentrations. The cells were cultured for 5 days to a confluency of about 70-80%. The cultured cells were harvested and washed with phosphate buffered saline (PBS), and then 10 mM Tris-HCl buffer (1 mL, pH 7.4) containing 2% sodium dodecyl sulfate (SDS) and 20 mM dithiothreitol (DTT) was added to the cells. The cell solution was then sonicated, boiled and centrifuged, and the resulting precipitate was suspended in PBS (1 mL) and measured for absorbance at 340 nm. Meanwhile, a portion of the solution after the sonication was taken and measured for its protein content, and the measured value was used as a standard for evaluating the degree of cell differentiation. A low-calcium (0.03 mM)-treated group and a high-calcium (1.2 mM)-treated group were used as the negative and positive control groups, respectively. The test result is shown in Table 9.

TABLE 9

| | Test materials | Differentiation of keratinocytes (%) |
|---|---|---|
| Control | Low-calcium-treated (0.03 mM $Ca^{2+}$) | 100 |
| | High-calcium-treated (1.2 mM $Ca^{2+}$) | 215 |
| Example 1 | 1 ppm | 117 |
| | 10 ppm | 122 |
| | 100 ppm | 125 |
| Example 2 | 1 ppm | 111 |
| | 10 ppm | 119 |
| | 100 ppm | 137 |
| Example 3 | 1 ppm | 97 |
| | 10 ppm | 109 |
| | 100 ppm | 121 |

From Table 9, it can be seen that the ginseng flower extract prepared in Example 1, the ginseng seed oil prepared in Example 2 and the ginseng seed residue extract prepared in Example 3 promoted the differentiation of keratinocytes. This suggests that can strengthen the skin moisturizing effect by maintaining the turnover cycles of removal of old keratinocytes and production of new keratinocytes at normal levels. Thus, the ginseng flower extract, the ginseng seed oil and the ginseng seed residue extract may facilitate the removal of the horny layer.

Test Example 10

Effect on Expression of Transglutaminase in Human Keratinocytes

Human keratinocytes were placed in a 96-well plate at a concentration of $5 \times 10^4$ cells/well and attached to the plate for 24 hours. The attached skin cells were treated with the test material, and after 2 days, the medium was removed, and the cells were stored in a refrigerator at −20° C. The cells were frozen and thawed twice, disrupted and treated with acetone/ethanol (1:1, v/v) and left to stand at 4° C. for 30 minutes to immobilize the cells. Then, the cells were left to stand at room temperature to evaporate the organic solvent and were blocked with 1% bovine serum albumin. The blocked cells were allowed to react with a transglutaminase antibody (primary antibody) and an HRP anti-mouse antibody (secondary antibody), and the color development of the cells was carried out by the addition of o-phenylenediamine (OPD). The expression level of transglutaminase in the cells was measured by measuring absorbance at 490 nm, and the correction was carried out based on background measurement at 630 nm. A low-calcium (0.03 mM)-treated group and a high-calcium (1.2 mM)-treated group were used as the negative and positive control groups, respectively. The test result is shown in Table 10.

TABLE 10

| | Test materials | Expression of transglutaminase (%) |
|---|---|---|
| Control | Low-calcium-treated(0.03mM$Ca^{2+}$) | 100 |
| | High-calcium-treated(1.2 mM$Ca^{2+}$) | 138 |
| Example 1 | 1 ppm | 98 |
| | 10 ppm | 119 |
| | 100 ppm | 141 |

From Table 10, it can be seen that the ginseng flower extract prepared in Example 1 according to the present disclosure showed superior expression of transglutaminase compared to the control group. This suggests that that the ginseng flower extract prepared in Example 1 according to the present disclosure improves the expression of transglutaminase.

Test Example 11

Increase in Skin Moisturizing Ability in Human

Seventy-five (75) men and women in their 50s and 60s with xeroderma were divided into three groups, and the faces of the subjects in each of the groups were applied with the creams of Example 4, Example 5 or Comparative Example 1 twice a day, for 4 weeks. Before the initiation of application, at 1 week, 2 weeks and 4 weeks after the initiation of application, and at 2 weeks after the end of application (after a total of 6 weeks), the moisture content of the skin of the subjects was measured with a corneometer under constant-temperature and constant-humidity conditions (24° C. and 40% relative humidity). The result is shown in Table 11. The test results were expressed as the percentages of increases in values relative to the corneometer values measured immediately before the initiation of application.

TABLE 11

| | Increase in water content (%) | | | |
|---|---|---|---|---|
| Test materials | After 1 week | After 2 weeks | After 4 weeks | After 6 weeks |
| Example 4 | 33 | 41 | 42 | 33 |
| Example 5 | 34 | 40 | 42 | 29 |
| Comparative Example 1 | 31 | 34 | 34 | 15 |

The corneometer is an instrument used to measure the moisture content of the skin by measuring the electrical conductivity of the epidermis. As shown in Table 11, the groups applied with the creams of Example 4 (containing the ginseng flower extract prepared in Example 1) and Example 5 (containing the ginseng seed oil prepared in Example 2 and the ginseng seed residue extract prepared in Example 3) showed more increase in the skin moisture content compared to the control group to which the cream of Comparative Example 1 was applied. Also, the skin moisture values measured at 2 weeks after the end of the application of the nourishing cream (after a total of 6 weeks) were similar to the skin moisture values, measured at 1-2 weeks after the initiation of application of the nourishing cream, for Example 4 or Example 5. This suggests that the application of the ginseng flower extract, the ginseng seed oil or the ginseng seed residue extract according to the present disclosure can maintain the skin moisture content for some period of time, even after the application thereof is stopped.

Test Example 12

Effect of Suppressing Sebum Secretion

The effect of relieving oily skin was measure as follows. The cream of Example 4 (containing the ginseng flower extract), Example 5 (containing the ginseng seed oil and the ginseng seed residue extract) or Comparative Example 1 was applied to the forehead of thirty (ten per each) women aged between 20 and 45 years twice a day (in the morning and evening). At week 1, week 2, week 3 and week 4 after the application, the sebum secretion of the skin was measured using a sebumeter (SM810). The experiment was carried out at 20° C. and relative humidity 20%. The result is shown in Table 12. The results are expressed as the average for the ten subjects. A value larger than 220 indicates oily skin, and a value between 100 and 220 indicates normal skin.

TABLE 12

| Test materials | Before application | Week 1 | Week 2 | Week 3 | Week 4 |
|---|---|---|---|---|---|
| Comparative Example 1 | 246 | 240 | 239 | 235 | 230 |
| Example 4 | 248 | 237 | 232 | 216 | 211 |
| Example 5 | 244 | 235 | 231 | 217 | 211 |

From Table 12, it can be seen that the nourishing cream of Example 4 containing the ginseng flower extract prepared in Example 1 and the nourishing cream of Example 5 containing the ginseng seed extract showed the effect of inhibiting the excessive secretion of sebum, suggesting that they had a sebum regulating effect. Thus, they may prevent acne and skin troubles resulting from the excessive sebum secretion.

Test Example 13

Inhibitory Effect Against Lipopolysaccharide (LPS)-Induced Cyclooxygenase-2 (COX-2) Biosynthesis Human fibroblasts were cultured in a 12-well culture plate at a concentration of $10^5$ cells, and then treated with LPS. Then, the culture medium was replaced with a medium containing 1 ppm, 10 ppm and 100 ppm of the ginseng flower extract prepared in Example 1 or with a medium containing 1 ppm and 50 ppm of the ginseng seed oil prepared in Example 2 or the ginseng seed residue extract prepared in Example 3. At 2 days of culture, the cells were harvested, and the amount of produced COX-2 was quantified using a Western blot method. The measurement results were calculated relative to 100 for the control using a densitometer. The result is shown in Table 13. The control group was not treated with the ginseng flower extract prepared in Example 1, the ginseng seed oil prepared in Example 2 or the ginseng seed residue extract prepared in Example 3.

TABLE 13

| Test material (ppm) | | COX-2 biosynthesis (%) |
|---|---|---|
| Example 1 | 100 | 56 |
| | 10 | 64 |
| | 1 | 89 |
| Example 2 | 50 | 42 |
| | 1 | 78 |
| Example 3 | 50 | 62 |
| | 1 | 89 |
| Control | | 100 |

From the results of Table 13, it could be seen that the ginseng flower extract prepared in Example 1, the ginseng seed oil prepared in Example 2 and the ginseng seed residue extract prepared in Example 3 according to the present disclosure reduced the biosynthesis of COX-2 induced by the inflammation-causing LPS in a concentration-dependent manner, suggesting that they are effective in relieving skin troubles.

Test Example 14

Effect of Relieving Acne and Skin Troubles

The face of 15 women with severe skin troubles including acne were washed with soap in a constant-temperature and constant-humidity room and adapted for 30 minutes. The numbers of acne lesions and inflammatory acne lesions were counted in order to measure the degree of skin troubles.

The test subjects were applied with each of the nourishing creams of Example 4, Example 5 and Comparative Example 1, and then the degree of acne and skin troubles was compared. The test result is shown in Table 14.

TABLE 14

| | Example 4 (n = 5) | Example 5 (n = 5) | Comparative Example 1 (n = 5) |
|---|---|---|---|
| Improvement of skin troubles | 86% | 84% | 32% |

As can be shown from the results of Table 14, when the cream of Example 4 containing the ginseng flower extract prepared in Example 1 or the cream of Example 5 containing the ginseng seed oil prepared in Example 2 and the ginseng seed residue extract prepared in Example 3 was applied for 4 weeks, the number of acne lesions was reduced and inflammatory troubles were relieved.

Test Example 15

Effect of Improving Human Skin (Facial) Complexion

To evaluate the effect of the ginseng flower extract of the present disclosure on the promotion of blood circulation in the skin, blood circulation in the skin was measured using a laser Doppler perfusion imager (LDPI). The LDPI is widely known as an instrument for measuring blood circulation in the skin and is a very sensitive device capable of measuring not only the rate and amount of blood flow in the capillary blood vessels of the skin but also the blood flow in small arteries and small veins.

The faces of test subjects were washed with soap in a constant-temperature and constant-humidity room and adapted for 30 minutes. Initial values were measured using the LDPI and an infrared (IR) camera as a skin temperature measuring device. The test subjects consisted of 40 women with cold hands and feet. The initial blood flow of the lower forehead portion was measured with the LDPI, and initial skin temperatures of the forehead, the portion under eyes and the cheek were measured using the IR camera.

After the creams of Examples 4 and 5 were applied to the test subjects for 1 week, the blood flow and skin temperature (° C.) of the subjects were compared with respect to the initial measurement values. The result is shown in Table 15.

TABLE 15

| | | Face (average) | Forehead | Under eyes | Cheek |
|---|---|---|---|---|---|
| Example 4 | Before application | 0.945 | 32.16 | 32.09 | 30.34 |
| | After 1 week (° C.) | 1.154 | 33.67 | 33.81 | 33.75 |
| Example 5 | Before application | 0.945 | 32.16 | 32.09 | 30.34 |
| | After 1 week (° C.) | 1.154 | 33.67 | 33.81 | 33.75 |

As can be seen from the table, when the cream of Example 4 containing the ginseng flower extract or the cream of Example 5 containing the ginseng seed oil and the ginseng seed residue extract was applied, the complexion of the face of the subjects was improved due to the improvement of peripheral blood circulation. This suggests that ginseng flower extract or the ginseng seed extract according to the present disclosure can effectively supply nutrients to the skin and can inhibit delay skin aging.

Examples 6-8 and Comparative Example 2

Compositions containing the ginseng flower extract prepared in Example 1, the ginseng seed oil prepared in Example 2 and the ginseng seed residue extract prepared in Example 3 were prepared as described in Table 16.

TABLE 16

| Components (wt%) | Ex. 6 | Ex. 7 | Ex. 8 | Comp. Ex. 2 |
|---|---|---|---|---|
| Ginseng flower extract (Example 1) | 10 | — | — | — |
| Ginseng seed oil (Example 2) | — | 10 | — | — |
| Ginseng seed residue extract (Example 3) | — | — | 0.1 | — |
| Capylic/capric triglyceride | 70 | 70 | 70 | 80 |
| Ethanol | 10 | 10 | 10 | 10 |
| Water | balance | balance | balance | balance |

Test Example 16

Effect of Preventing Hair Loss

The effect of preventing hair loss was tested for 30 subjects showing early signs of hair loss. The test was performed for 16 weeks. The subjects were asked to shampoo their hair using the compositions of Examples 6-8 and Comparative Example 2 once a day, for 16 weeks. After 16 weeks, the number of strands of hair falling during shampooing was counted. The result is shown in Table 17.

TABLE 17

| | Average/standard deviation of number of strands of falling hair |
|---|---|
| Comparative Example 2 | 82.80/10.32 |
| Example 6 (ginseng flower extract) | 75.07/8.70 |
| Example 7 (ginseng seed oil) | 76.27/9.10 |
| Example 8 (ginseng seed residue extract) | 79.21/6.10 |

As seen from Table 17, the number of strands of falling hair decreased significantly as compared to Comparative Example 2 when the composition containing the ginseng flower extract, the ginseng seed oil or the ginseng seed residue extract was used.

Test Example 17

Inhibitory Effect on Dandruff-Causing Fungus

In order to investigate the effect of the ginseng flower extract (Example 1), the ginseng seed oil (Example 2) and the ginseng seed residue extract (Example 3) on the dandruff-causing fungus Pityrosporum ovale (ATCC 12087), experiments were carried out using the broth dilution method. After performing double dilution, followed by incubation at 32° C. for 24 hours and stationary culturing at 48 hr, the lowest concentration at which no proliferation of the fungi was detected was determined as the minimum inhibition concentration (MIC). Microscopic observation was employed when visual examination was difficult because the medium was opaque. The result is shown in Table 18.

TABLE 18

| | MIC |
|---|---|
| Example 1 (ginseng flower extract) | 0.05% |
| Example 2 (ginseng seed oil) | 0.04% |
| Example 3 (ginseng seed residue extract) | 0.07% |

As seen from Table 18, the ginseng flower extract, the ginseng seed oil and the ginseng seed residue extract showed superior MIC's, suggesting that the ginseng flower extract, the ginseng seed oil and the ginseng seed residue extract may be effectively used to treat and prevent dandruff.

Test Example 18

Effect of Improving Hair Gloss

Hair sample (0.1 g) was washed with a shampoo (0.1 g) and then with flowing water. Then, the hair sample was dried at 25° C. and 50% humidity for 6 hours. Then, after applying 0.1 g of each of the compositions of Examples 6-8 and Comparative Example 2, as described in Table 16, gloss was measured using a goniophotometer as follows.

The gloss of the hair sample was measured using a goniophotometer equipped with a halogen lamp. The incidence angle is 30° and the reflection is between 0° and 90°. The gloss is calculated by the following equation.

$$\text{Gloss } (G) = Sf/d \quad \text{[Equation 4]}$$

Sf: Highest reflection (regular reflection)
d: Diffused reflection at 0°
Good gloss is characterized by less diffused reflection and more regular reflection. The measurement result is shown in Table 19.

TABLE 19

| | d | Sf | G |
|---|---|---|---|
| Comparative Example 2 | 6.49 | 68.41 | 10.54 |
| Example 6 (ginseng flower extract) | 3.58 | 83.20 | 23.24 |
| Example 7 (ginseng seed oil) | 2.81 | 87.45 | 31.12 |
| Example 8 (ginseng seed residue extract) | 3.91 | 64.23 | 16.43 |

As seen from Table 19, the composition comprising the ginseng flower extract or the ginseng seed extract showed significantly improved hair gloss over the Comparative Example 2.

Test Example 19

Effect of Promoting Differentiation of Adipocytes

Human bone marrow mesenchymal stem cells (hBM-MSCs) were purchased from Lonza, Inc. (Walkersville, Md., USA) and cultured according to the company's instructions. The mesenchymal stem cells were induced to differentiate into adipocytes according to the Lonza's instructions except for using troglitazone (TRO) instead of indomethacin. Specifically, the mesenchymal stem cells were cultured in a medium containing 1 g/mL insulin, 1 M dexamethasone (DEXA), 0.5 mM isobutylmethylxanthine (IBX) and 2 M TRO to induce them to differentiate into adipocytes. The test groups were treated with the ginseng flower extract prepared in Example 1, the ginseng seed oil prepared in Example 2 or the ginseng seed residue extract prepared in Example 3 as well as TRO and glibenclamide (Sigma-Aldrich, USA), each at 10 M (with 2-day intervals for 10 days). 10 days after the inducement of the differentiation into adipocytes, the culture medium was removed and the cells were washed with PBS and then immobilized for 10 minutes using 10% formalin/PBS (0.2 mL/cm$^2$). Thus immobilized cells were washed once with 60% isopropanol solution (0.5 mL/cm$^2$) and the lipids of the adipocytes were stained for 10 minutes using Oil Red 0 dissolved in 60% isopropanol (0.2 mL/cm$^2$). After the staining, Oil Red 0 was eluted by dissolving with 100% isopropanol solution and absorbance was measured at 500 nm. The result is shown in Table 20. The data were corrected relative to the IDX negative (−) control group.

TABLE 20

| | Relative staining of Oil Red O |
|---|---|
| Comparative Example | 1.00 |
| Example 1 (ginseng flower extract) | 2.18 |
| Example 2 (ginseng seed oil) | 2.74 |
| Example 3 (ginseng seed residue extract) | 1.75 |

As seen from Table 20, the ginseng flower extract and the ginseng seed extract promoted the differentiation of adipocytes (P value<0.01).

Hereinafter, formulation examples of the composition of the present disclosure will be described, but these formulation examples are illustrative only and are not intended to be limitative.

Formulation Example 1

Softening Lotion (Skin Lotion)

TABLE 21

| Components | Contents (wt %) |
|---|---|
| Purified water | balance |
| Ginseng flower extract or ginseng seed extract | 0.1 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Preservative, pigment and fragrance | qs |

Formulation Example 2

Nourishing Lotion (Milk Lotion)

TABLE 22

| Components | Contents (wt %) |
|---|---|
| Purified water | balance |
| Ginseng flower extract or ginseng seed extract | 0.1 |
| Beeswax | 4.0 |
| Polysorbate 60 | 1.5 |
| Sorbitan sesquioleate | 1.5 |
| Liquid paraffin | 0.5 |
| Montana 202 (Seppic) | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, pigment and fragrance | qs |

Formulation Example 3

Massage Cream

TABLE 23

| Components | Contents (wt %) |
|---|---|
| Purified water | balance |
| Ginseng flower extract or ginseng seed extract | 0.1 |
| Beeswax | 10.0 |
| Polysorbate 60 | 1.5 |
| PEG 60 hydrogenated castor oil | 2.0 |
| Sorbitan sesquioleate | 0.8 |
| Liquid paraffin | 40.0 |
| Squalane | 5.0 |
| Montana 202 (Seppic) | 4.0 |
| Glycerin | 5.0 |
| Butylene glycol | 3.0 |
| Propylene glycol | 3.0 |
| Triethanolamine | 0.2 |
| Preservative, pigment and fragrance | qs |

Formulation Example 4

Pack

TABLE 24

| Components | Contents (wt %) |
|---|---|
| Purified water | balance |
| Ginseng flower extract or ginseng seed extract | 0.1 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG-12 nonyl phenyl ether | 0.3 |
| Polysorbate 60 | 0.3 |
| Preservative, pigment and fragrance | qs |

The composition according to the present disclosure, which comprises the extract of ginseng flower or ginseng seed with different components and contents from those of ginseng root as an effective ingredient, may provide the effects of skin protection, anti-aging, anti-wrinkle, improvement of skin elasticity, skin whitening, skin moisturizing, prevention and improvement of skin dryness diseases such as atopy, removal of the horny layer, sebum control, anti-inflammation, prevention or improvement of skin troubles such as acne, improvement of skin complexion, prevention of hair loss, anti-dandruff, improvement of gloss and softness of hair, improvement of volume and elasticity of face or body, and improvement of facial or body line.

While the exemplary embodiments have been shown and described, it will be understood by those skilled in the art that various changes in form and details may be made thereto without departing from the spirit and scope of the present disclosure as defined by the appended claims.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A composition for external application for skin comprising a ginseng seed residue extract as an effective ingredient and a medium or base; wherein the ginseng is *Panax ginseng* C.A. Meyer.

2. The composition for external application for skin according to claim 1, wherein the composition further comprises one or more of a ginseng flower extract and a ginseng seed oil.

3. The composition for external application for skin according to claim 2, wherein the ginseng flower extract is comprised in an amount of 0.001 to 10 wt % based on the total weight of the composition for external application for skin.

4. The composition for external application for skin according to claim 1, wherein the ginseng seed residue extract is comprised in an amount of 0.001 to 10 wt % based on the total weight of the composition for external application for skin.

5. The composition for external application for skin according to claim 1, wherein the composition for external application for skin is used to protect skin by reducing skin damage.

6. The composition for external application for skin according to claim 5, wherein the composition for external application for skin protects the skin by reducing skin damage caused by oxidation or UV.

7. The composition for external application for skin according to claim 5, wherein the skin is the scalp or hair.

8. The composition for external application for skin according to claim 1, wherein the composition for external application for skin is used to improve skin aging.

9. The composition for external application for skin according to claim 8, wherein the composition for external application for skin suppresses skin aging through reduction of skin damage caused by oxidation or UV, promotion of collagen synthesis or inhibition of matrix metalloproteinase-1 (MMP-1) biosynthesis.

10. The composition for external application for skin according to claim 1, wherein the composition for external application for skin is used to improve wrinkles.

11. The composition for external application for skin according to claim 10, wherein the composition for external application for skin improves wrinkles through promotion of collagen synthesis or inhibition of matrix metalloproteinase-1 (MMP-1) biosynthesis.

12. The composition for external application for skin according to claim 1, wherein the composition for external application for skin is used to improve skin elasticity.

13. The composition for external application for skin according to claim 1, wherein the composition for external application for skin is used for skin whitening.

14. The composition for external application for skin according to claim 13, wherein the composition for external application for skin performs skin whitening through inhibition of melanin synthesis or depigmentation of skin pigmentation.

15. The composition for external application for skin according to claim 1, wherein the composition for external application for skin is used for skin moisturizing.

16. The composition for external application for skin according to claim 15, wherein the composition for external application for skin keeps the skin moisturized through promotion of differentiation of keratinocytes or promotion of expression of trans glutaminase.

17. The composition for external application for skin according to claim 15, wherein the composition for external application for skin is used to improve skin dryness diseases.

18. The composition for external application for skin according to claim 1, wherein the composition for external application for skin is used to remove of the horny layer.

19. The composition for external application for skin according to claim 1, wherein the composition for external application for skin is used to control skin sebum.

20. The composition for external application for skin according to claim 19, wherein the composition for external application for skin controls the skin sebum by suppressing excretion of sebum.

21. The composition for external application for skin according to claim 1, wherein the composition for external application for skin is used to improve inflammation or relieve irritation.

22. The composition for external application for skin according to claim 21, wherein the skin is the scalp.

23. The composition for external application for skin according to claim 1, wherein the composition for external application for skin is used to improve acne.

24. The composition for external application for skin according to claim 23, wherein the skin is the scalp.

25. The composition for external application for skin according to claim 1, wherein the composition for external application for skin is used to improve skin complexion.

26. The composition for external application for skin according to claim 1, wherein the skin is the scalp or hair.

27. The composition for external application for skin according to claim 26, wherein the composition for external application for skin is used to decrease hair loss.

28. The composition for external application for skin according to claim 26, wherein the composition for external application for skin is used for anti-dandruff purpose.

29. The composition for external application for skin according to claim 26, wherein the composition for external application for skin is used to improve gloss or softness of hair.

30. The composition for external application for skin according to claim 1, wherein the composition for external application for skin is used to improve volume and elasticity of face or body.

31. The composition for external application for skin according to claim 30, wherein the composition for external application for skin improves the volume and elasticity of face or body by promoting differentiation of adipocytes.

32. The composition for external application for skin according to claim 1, wherein the composition for external application for skin is used to improve facial or body line.

\* \* \* \* \*